United States Patent
Liu et al.

(10) Patent No.: US 11,672,751 B2
(45) Date of Patent: Jun. 13, 2023

(54) HAIR CARE COMPOSITION

(71) Applicant: Conopco, Inc., Englewood Cliffs, NJ (US)

(72) Inventors: Jingjing Liu, Shanghai (CN); Yingying Pi, Shanghai (CN); Raghupathi Subramanian, Trumbull, CT (US)

(73) Assignee: CONOPCO, INC., Englewood Cliffs, NJ (US)

( * ) Notice: Subject to any disclaimer, the term of this patent is extended or adjusted under 35 U.S.C. 154(b) by 56 days.

(21) Appl. No.: 16/762,046

(22) PCT Filed: Nov. 5, 2018

(86) PCT No.: PCT/EP2018/080114
§ 371 (c)(1),
(2) Date: May 6, 2020

(87) PCT Pub. No.: WO2019/096601
PCT Pub. Date: May 23, 2019

(65) Prior Publication Data
US 2020/0337980 A1  Oct. 29, 2020

(30) Foreign Application Priority Data

Nov. 17, 2017  (WO) ................. PCT/CN2017/111671
Dec. 14, 2017  (EP) ..................................... 17207292

(51) Int. Cl.
| | | |
|---|---|---|
| A61K 8/73 | (2006.01) | |
| A61K 8/27 | (2006.01) | |
| A61K 8/46 | (2006.01) | |
| A61K 8/49 | (2006.01) | |
| A61Q 5/00 | (2006.01) | |

(52) U.S. Cl.
CPC ............... *A61K 8/737* (2013.01); *A61K 8/27* (2013.01); *A61K 8/463* (2013.01); *A61K 8/4926* (2013.01); *A61Q 5/006* (2013.01); *A61K 2800/5426* (2013.01); *A61K 2800/58* (2013.01)

(58) Field of Classification Search
None
See application file for complete search history.

(56) References Cited

U.S. PATENT DOCUMENTS

| | | |
|---|---|---|
| 5,037,818 A | 8/1991 | Sime |
| 6,649,155 B1 | 11/2003 | Dunlop et al. |
| 2001/0051143 A1 | 12/2001 | Cottrell et al. |
| 2006/0104937 A1 | 5/2006 | Bailey et al. |
| 2013/0156715 A1 | 6/2013 | Hall et al. |
| 2014/0154200 A1 | 6/2014 | Lizarraga |
| 2016/0310393 A1 | 10/2016 | Chang et al. |
| 2018/0110714 A1* | 4/2018 | Glenn, Jr. ............... A61Q 5/02 |

FOREIGN PATENT DOCUMENTS

| | | |
|---|---|---|
| DE | 102007059705 | 6/2009 |
| EP | 0093601 | 10/1987 |
| GB | 2122214 | 1/1984 |
| JP | S58196300 | 11/1983 |
| JP | 2006516022 | 6/2006 |
| WO | WO9509599 | 4/1995 |
| WO | WO9631188 | 10/1996 |
| WO | WO9726854 | 7/1997 |
| WO | WO9850007 | 11/1998 |
| WO | WO9918929 | 4/1999 |
| WO | WO9938476 | 8/1999 |
| WO | WO9939683 A1 | 8/1999 |
| WO | WO0197761 | 12/2001 |
| WO | WO03088932 | 10/2003 |
| WO | WO03088940 | 10/2003 |
| WO | WO03094874 | 11/2003 |
| WO | WO2004035015 | 4/2004 |
| WO | WO2004105711 | 12/2004 |
| WO | WO2006036510 | 4/2006 |
| WO | WO2008079317 | 7/2008 |
| WO | WO2010040671 | 4/2010 |
| WO | WO2012022553 | 2/2012 |
| WO | WO2013011122 | 1/2013 |

(Continued)

OTHER PUBLICATIONS

Search Report and Written Opinion in PCTEP2018056061; dated May 11, 2018.

(Continued)

*Primary Examiner* — David J Blanchard
*Assistant Examiner* — Sarah J Chickos
(74) *Attorney, Agent, or Firm* — Foley & Lardner LLP

(57) ABSTRACT

A hair care composition is disclosed comprising a cationically modified guar polymer having a cationic degree of substitution of from 0.35 to 0.70, an ethoxylated alkyl sulfate anionic surfactant having a formula $RO(CH_2CH_2O)_n SO_3M$, wherein R is an alkyl or alkenyl group having from 8 to 18 carbon atoms; M is a solubilising cation comprising sodium, potassium, 5 ammonium, substituted ammonium or mixtures thereof; n is the degree of ethoxylation of from 0.5 to 3 and from 0.01 to 10% by weight of an anti-dandruff agent selected from azole based anti-fungal agents, piroctone olamine, metal pyrithione salts, selenium sulfide or mixtures thereof; wherein the degree of substitution is measured using $^1$H NMR and the spectrum is recorded at 25° C.

19 Claims, No Drawings

(56) References Cited

FOREIGN PATENT DOCUMENTS

WO     WO2015055432     4/2015
WO     WO2016172409     10/2016

OTHER PUBLICATIONS

Search Report in EP17207292; dated May 14, 2018; European Patent Office (EPO).
Search Report and Written Opinion in PCTEP2018080114; dated Jan. 7, 2019.
IPRP2 in PCTEP2018080114; dated Oct. 1, 2019.
Notice of Opposition in EP18796665 (EP3709960); Jun. 28, 2022; European Patent Office (EPO).
Lamberti Spa—BU Home & Personal Care; Cesmetic BF 7; Technical Bulletin Safety Data Sheet; Jul. 2015; PP1; Italy.

\* cited by examiner

HAIR CARE COMPOSITION

CROSS REFERENCE TO RELATED APPLICATION

This application is a U.S. National Stage Application under 35 U.S.C. § 371 of International Application No. PCT/EP2018/080114, filed on Nov. 5, 2018, which claims the benefit of International Application No. PCT/CN2017/111671, filed on Nov. 17, 2017 and European Application No. 17207292.8 on Dec. 14, 2017, the entire disclosures of which are hereby incorporated by reference for any and all purposes.

TECHNICAL FIELD OF THE INVENTION

This invention relates to a hair care composition, especially a hair care composition comprising a cationically modified guar polymer, a specific anionic surfactant and anti-dandruff agents that results in enhanced anti-dandruff delivery efficiency on hair/scalp to ensure maximum antimicrobial efficacy.

BACKGROUND OF THE INVENTION

Hair care compositions generally provide cleansing or conditioning benefits or a combination of the two. Such compositions typically comprise one or more cleansing surfactants which generally aid in cleaning the hair and the scalp free of undesirable soil, particles and fatty matter. Conditioning benefit is achieved by including one or more conditioning agents in the hair care composition. Conditioning benefit is delivered with an oily material being deposited onto the hair resulting in the formation of a film, which makes the hair easier to comb when wet and more manageable when dry.

Additionally, anti-dandruff benefit has been provided through hair care compositions. Dandruff is an issue that affects many people globally. The condition is manifested by the shedding of clumps of dead skin cells from the scalp. These are white in colour and provide an aesthetically displeasing appearance. A factor that contributes to dandruff is certain members of the Malassezia yeasts. To combat these, anti-dandruff products have included certain anti-dandruff agents which have anti-fungal activity, for example zinc pyrithione. Such a product has to perform as a hair cleansing shampoo, while mitigating the causes of dandruff. Therefore, it is always desired to improve the delivery efficiency of anti-dandruff agents to maximize the effectiveness of such anti-dandruff agents. Typical anti-dandruff agents used in hair care are metal pyrithione salts e.g zinc pyrithione, piroctone olamine (octopirox), azole based anti-fungal agents (e.g. climbazole), selenium sulfide and combinations thereof. Of these, zinc pyrithione is a particulate material.

However, it is usually difficult to achieve high delivery of anti-dandruff agents from hair care composition. Those anti-dandruff agents do not strongly adhere to scalp surfaces which makes them easy to be rinsed off during hair wash or shower.

There is a continuing need for solving the problem of dandruff by enhancing the delivery efficiency of anti-dandruff agents. Cationic polymers are often used to enhance the deposition of the conditioning agent and/or anti-dandruff agents onto the hair and/or scalp. These polymers may be synthetic or natural polymers that have been modified with cationic substituents. The present inventors have now found unexpectedly that the delivery efficiency of anti-dandruff agents can be enhanced by using a combination of a cationically modified guar polymer of a specific cationic degree of substitution and an ethoxylated anionic surfactant with a specific degree of ethoxylation in a hair care composition.

Additional Information

U.S. Pat. No. 6,649,155 B1 discloses shampoo compositions that provide a superior combination of anti-dandruff efficacy and conditioning, and a method of cleansing and conditioning the hair comprising applying to the hair an effective amount of said compositions.

The additional information above does not describe a hair care composition comprising a cationically modified guar polymer having a cationic degree of substitution of from 0.35 to 0.70, an ethoxylated alkyl sulfate anionic surfactant having a formula $RO(CH_2CH_2O)_nSO_3M$, wherein R is an alkyl or alkenyl group having from 8 to 18 carbon atoms; M is a solubilising cation comprising sodium, potassium, ammonium, substituted ammonium or mixtures thereof; n is the degree of ethoxylation of from 0.5 to 3 and from 0.01 to 10% by weight of an anti-dandruff agent selected from azole based anti-fungal agents, piroctone olamine, metal pyrithione salts, selenium sulfide or mixtures thereof, and especially such a hair care composition can enhance the delivery efficiency of anti-dandruff agents; wherein the degree of substitution is measured using $^1H$ NMR and the spectrum is recorded at 25° C.

Tests and Definitions

Hair Care Composition

"Hair care composition", as used herein, is meant to include a composition for topical application to hair and/or scalp of mammals, especially humans. Such a composition may be generally classified as leave-on or rinse off, and includes any product applied to a human body for also improving appearance, cleansing, odor control or general aesthetics. The composition of the present invention can be in the form of a liquid, lotion, cream, foam, scrub, gel, or bar. Non-limiting examples of such compositions include leave-on hair lotions, creams, and rinse-off shampoos, conditioners, shower gels, or toilet bar. The composition of the present invention is preferably a rinse-off composition, especially preferred being a shampoo or a conditioner and most preferably a shampoo.

Degree of Substitution

"Degree of substitution", as used herein, refers to the average number of moles of cationic groups per mole of sugar unit. The degree of substitution (DS) is measured using $^1H$ NMR in a solvent of deuterium oxide ($D_2O$) and deuterium chloride (DCl) mixture. For example, the DS of guar hydroxylpropyltrimonium chloride is measured using $^1H$ NMR and the spectrum is recorded at 25° C. The sample for measurement using NMR is prepared as follows. The polymer sample is dispersed in $D_2O$ and DCl solution with stirring, and then put into a boiling water bath for one hour. After cooling to the room temperature, the sample is filtered and the clear filtrate is poured into an NMR tube.

The peak corresponding to the nine methyl protons of the quaternary ammonium group on guar units, which appears between 3.1-3.3 ppm, is integrated as A1. The multiplet of peaks corresponding to the anomeric protons on sugar ring and protons on $CH_2$ and CH groups of the cationic substituent, which appear between 3.3-4.5 ppm, are also integrated as A2. Therefore, the DS for the case of the cationizing agent 2,3-epoxypropyltrimethylammonium chloride may be calculated as follows:

$$DS = \frac{(A1/9)}{(A2 - A1 \times 5/9)/6}$$

Cationic Charge Density

"Cationic charge density", as used herein, refers to the number of cationic charges per weight unit of a given polymer. Cationic charge density can be calculated from the degree of substitution as described in WO 2013/011122, the disclosure of which is hereby incorporated by reference in its entirety but especially page 8 lines 8-17. For example, for cationically-modified guar polymer obtained by reacting with 2,3-epoxypropyltrimethylammonium chloride, the cationic charge density may be calculated from the DS using the following equation:

Cationic charge density in milliequivalents per gram (meq/g) =

$$\frac{DS \times 1000}{162 + 151 \times DS}$$

Degree of Ethoxylation

"Degree of Ethoxylation", as used herein, refers to the average number of moles of ethylene oxide unit per mole of ethoxylated product. The degree of ethoxylation is measured using $^1$H NMR in a solvent of deuterium oxide ($D_2O$). For example, the degree of ethoxylation of sodium lauryl ether sulfate (SLES) is measured using $^1$H NMR (Bruker-Biospin, 400 MHz) and the spectrum is recorded at 25° C. The sample for measurement using NMR is prepared as follows: the sample is dispersed in $D_2O$ in a centrifugal tube and sonicated, then the solution is filtered and transferred to an NMR tube. The peaks corresponding to the protons of the sample appear at about 3.98 ppm, about 4.15 ppm and between about 3.58 to about 3.84 ppm. The peaks corresponding to the protons for —$CH_2$—, which appear at about 4.15 ppm and about 3.98 ppm, are integrated as A3. The peaks corresponding to the four protons for —$OCH_2CH_2$—, which appear at 4.15 ppm and between about 3.58 to about 3.84 ppm, are also integrated as A4. The degree of ethoxylation of SLES may be calculated as follows:

$$\text{The degree of ethoxylation} = \frac{(A4/4)}{(A3/2)}$$

Average Particle Size:

"Average particle size", as used herein, refers to the volume average particle size as measured using light scattering technique with a Malvern Mastersizer 2000 instrument. The settings used for the measurement included a particle absorption of 0.1, with water as the dispersant an obscuration limit of 10-12% and a pump-speed of 960 rpm. The average particle size of a sample was measured from the particle size distribution curves as an average of three sample readings.

Water-Insoluble

"Water-insoluble", as used herein, refers to the solubility of a material in water at 25° C. and atmospheric pressure being 0.1% by weight or less.

Molecular Weight

"Molecular weight", as used herein, refers to the weight average molecular mass of a given polymer. The weight average molecular weight (WAVG MW) of cationic guar gum herein is determined by SEC (Size Exclusion Chromatography) analysis using absolute calibration (universal calibration). Polysaccharide standards pulluan and dextran were used for calibration.

Miscellaneous

Except in the examples, or where otherwise explicitly indicated, all numbers in this description indicating amounts of material or conditions of reaction, physical properties of materials and/or use may optionally be understood as modified by the word "about".

All amounts are by weight of the final oral care composition, unless otherwise specified. It should be noted that in specifying any ranges of values, any particular upper value can be associated with any particular lower value.

For the avoidance of doubt, the word "comprising" is intended to mean "including" but not necessarily "consisting of" or "composed of". In other words, the listed steps or options need not be exhaustive.

The disclosure of the invention as found herein is to be considered to cover all embodiments as found in the claims as being multiply dependent upon each other irrespective of the fact that claims may be found without multiple dependency or redundancy.

Where a feature is disclosed with respect to a particular aspect of the invention (for example a composition of the invention), such disclosure is also to be considered to apply to any other aspect of the invention (for example a method of the invention) *mutatis mutandis*.

SUMMARY OF THE INVENTION

In a first aspect, the present invention is directed to a hair care composition comprising:

a) a cationically modified guar polymer having a cationic degree of substitution of from 0.35 to 0.70;

b) an ethoxylated alkyl sulfate anionic surfactant having a formula $RO(CH_2CH_2O)_nSO_3M$, wherein R is an alkyl or alkenyl group having from 8 to 18 carbon atoms; M is a solubilising cation comprising sodium, potassium, ammonium, substituted ammonium or mixtures thereof; n is the degree of ethoxylation of from 0.5 to 3;

c) from 0.01 to 10% by weight of an anti-dandruff agent selected from azole based antifungal agents, piroctone olamine, metal pyrithione salts, selenium sulfide or mixtures thereof;

wherein the degree of substitution is measured using $^1$H NMR and the spectrum is recorded at 25° C.

In a second aspect, the present invention is directed to a packaged hair care product comprising the hair care composition of the first aspect of this invention.

In a third aspect, the present invention is directed to a method of depositing anti-dandruff agents onto scalp comprising the step of applying the hair care composition of any embodiment of the first aspect of this invention onto scalp surfaces of an individual.

All other aspects of the present invention will more readily become apparent upon considering the detailed description and examples which follow.

DETAILED DESCRIPTION

It has now been found that a hair care composition comprising a combination of a cationically modified guar polymer of specific cationic degree of substitution and an ethoxylated anionic surfactant with a specific degree of ethoxylation can enhance the delivery efficiency of anti-dandruff agents on scalp surfaces. Delivery efficiency, as used herein, means the ability to deliver and deposit anti-dandruff agents on scalp surfaces of an individual.

The cationically modified guar polymer suitable for use in compositions of the present invention is preferably guar hydroxypropyltrimonium chloride. Guar polymer predominantly contains galactomannan polymer chains. This polymer is available at various molecular weights and degree of cationic substitutions depending on how much the guar has been hydrolysed and cationised.

Generally for cationic polysaccharide polymers, the hydroxyl groups of the non-modified monomeric sugar ring units are the sites for cationic substitution. Degree of substitution (DS) is typically in the range from 0 to 3 due to the fact that the monomeric sugar unit of most polysaccharide has in average three hydroxyl groups available for substitution. In addition to the DS, the cationic charge on polymers can also be quantified as cationic charge density. DS has previously been determined by different methods. For example, the cationic charge density of the polymer has in some cases been calculated based on a percent nitrogen content determined via the Kjeldahl method as described in US Pharmacopoeia under chemical tests for nitrogen determination and is expressed in milliequivalents (meq) per gram. The cationic charge density of the polymer in the present invention is, however, calculated from the DS, which is measured by $^1$H NMR in a solvent of deuterium oxide ($D_2O$) and deuterium chloride (DCl) mixture.

In many cases the DS obtained from $^1$H NMR measurement may not be suitable to be compared with that obtained from Kjeldahl method, due to the fact that the two methods are influenced by different factors. For example, Jaguar C17 from Rhodia has a DS of 0.18 (cationic charge density of 1.0 meq/g) measured by $^1$H NMR but it has a DS of 0.34 (cationic charge density of 1.6 meq/g) measured by Kjeldahl method.

The cationically modified guar polymer according to the invention has a DS of from 0.35 to 0.70, preferably from 0.40 to 0.65, more preferably from 0.45 to 0.60. Typically, the cationically modified guar polymer has a molecular weight of from 100,000 gram per mole (g/mol) to 2,300,000 g/mol, more preferably from 150,000 g/mol to 2,000,000 g/mol, and most preferably from 300,000 g/mol to 1,600,000 g/mol.

Typically, the hair care composition of the present invention comprises the cationically modified guar polymer in an amount of from 0.001 to 1% by weight of the hair care composition, more preferably from 0.01 to 0.5%, and most preferably from 0.03 to 0.3%, based on the total weight of the total weight of the hair care composition and including all ranges subsumed therein.

The hair care composition of the present invention also comprises an ethoxylated anionic surfactant which is an ethoxylated alkyl sulfate anionic surfactant having a formula $RO(CH_2CH_2O)_nSO_3M$, wherein R is an alkyl or alkenyl group having from 8 to 18 (preferably 12 to 18) carbon atoms, M is a solubilising cation comprising sodium, potassium, ammonium, substituted ammonium or mixtures thereof, n is the degree of ethoxylation of from 0.5 to 3, preferably from 1 to 3, more preferably from 1.5 to 3, most preferably 2. An example is sodium lauryl ether sulfate (SLES).

Preferred ethoxylated alkyl sulfate anionic surfactant is sodium lauryl ether sulfate (SLES) having a degree of ethoxylation of from 0.5 to 3, preferably from 1 to 3, more preferably from 1.5 to 3, and most preferably 2.

Generally, the ethoxylated alkyl sulfate anionic surfactant in hair care composition of the present invention ranges from 0.5 to 45%, more preferably from 1 to 30%, and most preferably from 5 to 20%, based on the total weight of the hair care composition and including all ranges subsumed therein.

Typically, the hair care composition comprises the cationically modified guar polymer and the ethoxylated alkyl sulfate anionic surfactant in a weight ratio from 1:200 to 1:1, more preferably from 1:150 to 1:10, and most preferably from 1:100 to 1:30.

The hair care composition further comprises anti-dandruff agents, which are compounds that are active against dandruff and are typically anti-microbial agents and preferably anti-fungal agents.

Suitable anti-dandruff agents include compounds selected from azole based anti-fungal agents, piroctone olamine, metal pyrithione salts, selenium sulfide or mixtures thereof, preferably azole based anti-fungal agents, metal pyrithione salts, piroctone olamine or mixtures thereof. The preferred azole based anti-fungal agents are ketoconazole and climbazole. Preferred metal pyrithione salts are zinc, copper, silver and zirconium pyrithione. Most preferably, the antidandruff agent comprises zinc pyrithione, climbazole, piroctone olamine or mixtures thereof.

In an especially preferred embodiment, the antidandruff agent is zinc pyrithione. Preferably, zinc pyrithione is particulate having a D50 particle size of from 0.25 to 8 microns, more preferably from 0.5 to 8 microns, more preferably still from 1.0 to 5 microns, and most preferably from 1 to 3 microns. Zinc pyrithione as per the above particle size is available from Kolon Life Science Inc., Sino Lion (USA) Ltd, Lonza and other suppliers.

The hair care composition of the invention comprises anti-dandruff agent in an amount of from 0.01 to 10%, preferably from 0.01 to 5%, more preferably from 0.05 to 2%, and most preferably from 0.05 to 1.5%, based on the total weight of the hair care composition and including all ranges subsumed therein.

Without wishing to be bound by theory, the present inventors believe that the combination of a cationically modified guar polymer of the specific DS and an ethoxylated anionic surfactant with the specific degree of ethoxylation provides controlled flocculation within a hair care product like shampoo, which generates less aggregates of anti-dandruff agents so ensures their evenly dispersity and better retention on scalp surfaces after rinsing thereby leading to higher deposition.

The pH of the composition is preferably equal to or higher than 4.0, more preferably in the range of 5.0 to 7.0.

In addition to the cationically modified guar polymer, the hair care composition may further comprise a minor amount of other cationic polymers. The other cationic polymer may be a homopolymer or be formed from two or more types of monomers. The molecular weight of the polymer will generally be between 5,000 and 10,000,000 g/mol, typically at least 10,000 g/mol and preferably from 100,000 to 2,000,000 g/mol. The polymers will have cationic nitrogen containing groups such as quaternary ammonium or protonated amino groups, or a mixture thereof.

The cationic nitrogen containing group will generally be present as a substituent on a fraction of the total monomer units of the cationic polymer. The ratio of the cationic to non-cationic monomer units is selected to give polymers having a DS in the required range.

Suitable further cationic polymers include, for example, copolymers of vinyl monomers having cationic amine or quaternary ammonium functionalities with water soluble spacer monomers such as (meth)acrylamide, alkyl and dialkyl(meth)acrylamides, alkyl(meth)acrylate, vinyl caprolactone and vinyl pyrrolidine. The alkyl and dialkyl substituted monomers preferably have C1-C7 alkyl groups, more preferably C1-3 alkyl groups. Other suitable spacers include vinyl esters, vinyl alcohol, maleic anhydride, propylene glycol and ethylene glycol. Preferably, the further cationic polymer is cationic polysaccharide polymers, such as cationic cellulose derivatives, cationic starch derivatives and mixtures thereof.

The hair care composition may further comprise one or more cleansing surfactants in addition to the ethoxylated alkyl sulfate anionic surfactant that is included in the composition. Preferably, the cleansing surfactants are anionic surfactants.

Examples of suitable anionic cleansing surfactants are the alkyl sulphates, alkaryl sulphonates, alkanoyl isethionates, alkyl succinates, alkyl sulphosuccinates, alkyl ether sulphosuccinates, N-alkyl sarcosinates, alkyl phosphates, alkyl ether phosphates, and alkyl ether carboxylic acids and salts thereof, especially their sodium, magnesium, ammonium and mono-, di- and triethanolamine salts. The alkyl and acyl groups generally contain from 8 to 18, preferably from 10 to 16 carbon atoms and may be unsaturated. The alkyl ether sulphosuccinates, alkyl ether phosphates and alkyl ether carboxylic acids and salts thereof may contain from 1 to 20 ethylene oxide or propylene oxide units per molecule.

Typical anionic cleansing surfactants for use in hair care compositions of the invention include sodium oleyl succinate, ammonium lauryl sulphosuccinate, sodium lauryl sulphate, sodium lauryl ether sulphosuccinate, ammonium lauryl sulphate, sodium dodecylbenzene sulphonate, triethanolamine dodecylbenzene sulphonate, sodium cocoyl isethionate, sodium lauryl isethionate, lauryl ether carboxylic acid and sodium N-lauryl sarcosinate.

Suitable preferred additional anionic cleansing surfactants are sodium lauryl ether sulphosuccinate(n)EO, (where n is from 1 to 3), lauryl ether carboxylic acid (n) EO (where n is from 10 to 20).

Mixtures of any of the foregoing anionic cleansing surfactants may also be suitable.

Generally, the total amount of additional anionic cleansing surfactant in hair care composition of the present invention ranges from 0.5 to 45%, more preferably from 1.5 to 35% and most preferably from 5 to 20%, based on the total weight of the hair care composition and including all ranges subsumed therein.

In an especially preferred embodiment, the hair care composition may further comprise co-surfactants such as amphoteric and zwitterionic surfactants to provide mildness to the composition.

Examples of amphoteric or zwitterionic surfactants include alkyl amine oxides, alkyl betaines, alkyl amidopropyl betaines, alkyl sulphobetaines (sultaines), alkyl glycinates, alkyl carboxyglycinates, alkyl amphoacetates, alkyl amphopropionates, alkylamphoglycinates, alkyl amidopropyl hydroxysultaines, acyl taurates and acyl glutamates, wherein the alkyl and acyl groups have from 8 to 19 carbon atoms. Typical amphoteric and zwitterionic surfactants for use in compositions of the invention include lauryl amine oxide, cocodimethyl sulphopropyl betaine, lauryl betaine, cocamidopropyl betaine and sodium cocoamphoacetate. Preferably, the co-surfactant is cocamidopropyl betaine (CAPB).

Typically, co-surfactant may be present in hair care compositions of the invention in an amount from 0.5 to 8% by weight of the hair care composition, preferably from 1 to 4%, based on the total weight of the hair care composition and including all ranges subsumed therein.

The hair care composition may additionally comprise a conditioning agent to provide conditioning benefit. Typically, the most popular conditioning agents used in hair care compositions are water-insoluble oily materials such as mineral oils, naturally occurring oils such as triglycerides and silicone polymers. Conditioning benefit is achieved by the oily material being deposited onto the hair resulting in the formation of a film, which makes the hair easier to comb when wet and more manageable when dry. Preferably, the conditioning agent is non-volatile, meaning that it has a vapour pressure of less than 1000 Pa at 25° C.

Preferably, the hair care composition comprises discrete dispersed droplets of a water-insoluble conditioning agent, which has a mean droplet diameter ($D_{3,2}$) of less than 15 microns, preferably less than 10 microns, more preferably less than 5 microns, most preferably less than 3 microns. The mean droplet diameter ($D_{3,2}$) of a water-insoluble conditioning agent may be measured by means of a laser light scattering technique, for example using a 2600D Particle Sizer from Malvern Instruments.

The water-insoluble conditioning agent may include non-silicone conditioning agent comprising non-silicone oily or fatty materials such as hydrocarbon oils, fatty esters and mixtures thereof. Preferably, the water-insoluble conditioning agent is emulsified silicone oil.

Suitable silicones include polydiorganosiloxanes, in particular polydimethylsiloxanes which have the CTFA designation dimethicone. Also suitable for use in compositions of this invention (particularly shampoos and conditioners) are polydimethyl siloxanes having hydroxyl end groups, which have the CTFA designation dimethiconol. Also suitable for use in compositions of this invention are silicone gums having a slight degree of cross-linking, as are described for example in WO 96/31188. Preferably, the silicone oil comprises dimethicone, dimethiconol or a mixture thereof.

The viscosity of the emulsified silicone itself (not the emulsion or the final hair care composition) is typically at least 10,000 cSt (centi-Stokes=$mm^2 \cdot S^{-1}$) at 25° C., preferably at least 60,000 cSt, most preferably at least 500,000 cSt, ideally at least 1,000,000 cSt. Preferably the viscosity does not exceed $10^9$ cSt for ease of formulation. Suitable methods for measuring the kinematic viscosity of silicone oils are known to those skilled in the art, e.g. capillary viscometers. For high viscosity silicones, a constant stress rheometer can be used to measure viscosity.

Suitable emulsified silicones for use in the hair care compositions of this invention are available as pre-formed silicone emulsions from suppliers of silicones such as Dow Corning and GE silicones. The use of such pre-formed silicone emulsion is preferred for ease of processing and control of silicone particle size. Such pre-formed silicone emulsions will typically additionally comprise a suitable emulsifier, and may be prepared by a chemical emulsification process such as emulsion polymerisation, or by mechanical emulsification using a high shear mixer.

Examples of suitable pre-formed silicone emulsions include DC1785, DC1788, DC7128, all available from Dow Corning. These are emulsions of dimethiconol/dimethicone.

Another class of silicones which may be used are functionalized silicones such as amino functional silicones, meaning a silicone containing at least one primary, secondary or tertiary amine group, or a quaternary ammonium group. Examples of suitable amino functional silicones include polysiloxanes having the CTFA designation "amodimethicone."

Preferably, silicone emulsion droplets are blended with certain types of surface active block polymers of a high molecular weight to form silicone emulsions, as described for example in WO03/094874. One preferred form of the surface active block polymer having polyoxypropylene and polyoxyethylene groups as the hydrophobic and hydrophilic part respectively has formula I and has the CTFA designation poloxamer, known commercially under the trade name "Pluronic" from BASF.

I)  $HO(CH_2CH_2O)_x(CH(CH_3)CH_2O)_y(CH_2CH_2O)_xH$

Suitably, the mean value of x in formula I is 4 or more, preferably 8 or more, more preferably 25 or more, yet more preferably 50 or more and most preferably 80 or more. The mean value of x is typically no greater than 200. Suitably, the mean value of y is 25 or more, preferably 35 or more, more preferably 45 or more and most preferably 60 or more. The mean value of y is typically no greater than 100.

Another preferred form of the surface active block polymer is according to formula II and has the CTFA designation Poloxamine. Those are commercially available under the trade name "Tetronic" from BASF.

II) 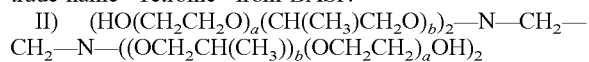 $(HO(CH_2CH_2O)_a(CH(CH_3)CH_2O)_b)_2-N-CH_2-CH_2-N-((OCH_2CH(CH_3))_b(OCH_2CH_2)_aOH)_2$ Suitably, the mean value of a is 2 or more, preferably 4 or more, more preferably 8 or more, even more preferably 25 or more and most preferably 40 or more. The mean value of a is typically no greater than 200. The mean value of b is suitably 6 or more, preferably 9 or more, more preferably 11 or more and most preferably 15 or more. The mean value of b is typically no greater than 50.

Preferably, the surface active block polymer is poloxamer and/or poloxamine, more preferably, the surface active block polymer is poloxamer.

Preferably, the surface active block polymer is blended with dimethicone. The weight ratio of dimethicone to surface active block polymer in the blend is preferably in the range from 2:1 to 200:1, more preferably from 5:1 to 50:1, even more preferably from 10:1 to 40:1, most preferably from 15:1 to 30:1.

The water-insoluble conditioning agent is generally present in hair care composition of this invention in an amount from 0.05 to 15%, preferably from 0.1 to 10%, more preferably from 0.5 to 8%, most preferably from 1 to 5%, based on the total weight of the hair care composition and including all ranges subsumed therein.

Preferably the composition of the invention further comprises a suspending agent. Suitable suspending agents are selected from polyacrylic acids, cross-linked polymers of acrylic acid, copolymers of acrylic acid with a hydrophobic monomer, copolymers of carboxylic acid-containing monomers and acrylic esters, cross-linked copolymers of acrylic acid and acrylate esters, heteropolysaccharide gums and crystalline long chain acyl derivatives. The long chain acyl derivative is desirably selected from ethylene glycol stearate, alkanolamides of fatty acids having from 16 to 22 carbon atoms and mixtures thereof. Ethylene glycol distearate and polyethylene glycol 3 distearate are preferred long chain acyl derivatives, since these impart pearlescence to the composition. Polyacrylic acid is available commercially as Carbopol 420, Carbopol 488 or Carbopol 493. Polymers of acrylic acid cross-linked with a polyfunctional agent may also be used; they are available commercially as Carbopol 910, Carbopol 934, Carbopol 941 and Carbopol 980. An example of a suitable copolymer of a carboxylic acid containing monomer and acrylic acid esters is Carbopol 1342. All Carbopol (trademark) materials are available from Goodrich.

Suitable cross-linked polymers of acrylic acid and acrylate esters are Pemulen TR1 or Pemulen TR2. A suitable heteropolysaccharide gum is xanthan gum, for example that available as Kelzan mu.

Mixtures of any of the above suspending agents may be used. Preferred is a mixture of cross-linked polymer of acrylic acid and crystalline long chain acyl derivative.

The suspending agent is generally present in hair care composition of this invention in an amount of from 0.1 to 10%, more preferably from 0.5 to 6%, and most preferably from 0.5 to 4%, based on the total weight of the hair care composition and including all ranges subsumed therein.

Preservatives may also be incorporated into the hair care composition of this invention to protect against the growth of potentially harmful microorganisms. Suitable traditional preservatives include alkyl esters of parahydroxybenzoic acid, hydantoin derivatives, propionate salts, and a variety of quaternary ammonium compounds. Illustrative yet non-limiting examples of the types of preservatives that may be used in this invention include, for examples, phenoxyethanol, sodium salicylate, methyl paraben, butyl paraben, propyl paraben, diazolidinyl urea, sodium dehydroacetate, benzyl alcohol, sodium benzoate, iodopropynyl butylcarbamate, caprylyl glycol, disodium EDTA or mixtures thereof. In an especially preferred embodiment, the preservative is phenoxyethanol, sodium salicylate or a mixture thereof. Preservatives are preferably employed in amounts ranging from 0.01 to 2% by weight of the hair care composition.

The hair care composition of the present invention may contain other ingredients which are common in the art to enhance physical properties and performances. Suitable ingredients include but are not limited to fragrance, dyes and pigments, pH adjusting agents, pearlescers or opacifiers, viscosity modifiers, thickeners, and natural hair nutrients such as botanicals, fruit extracts, sugar derivatives and amino acids.

The compositions of the invention are primarily intended for topical application to scalp and/or at least a portion of the hair of an individual, either in rinse-off or leave-on compositions, preferably in rinse-off compositions like shampoos.

The following examples are provided to facilitate an understanding of the present invention. The examples are not provided to limit the scope of the claims.

EXAMPLES

Example 1

This example demonstrated the effect of DS of guars on the deposition of anti-dandruff agents onto scalp surfaces. Compositions were prepared according to the formulations detailed in Tables 1, 2, and 3. All ingredients are expressed weight percent of the total formulation, and as level of active ingredient.

TABLE 1

| | Samples | | | |
|---|---|---|---|---|
| Ingredient | 1 | 2 | 3 | 4 |
| Water | Balance | Balance | Balance | Balance |
| Sodium lauryl ether sulfate (2EO) | 14 | 14 | 14 | 14 |
| Carbopol 980 | 0.6 | 0.6 | 0.6 | 0.6 |
| Guar hydroxypropyltrimonium chloride$^a$ | 0.2 | — | — | — |

TABLE 1-continued

| Ingredient | Samples | | | |
|---|---|---|---|---|
| | 1 | 2 | 3 | 4 |
| Guar hydroxypropyltrimonium chloride[b] | — | 0.2 | — | — |
| Guar hydroxypropyltrimonium chloride[c] | — | — | 0.2 | — |
| Guar hydroxypropyltrimonium chloride[d] | — | — | — | 0.2 |
| Zinc pyrithione (ZPTO) | 0.96 | 0.96 | 0.96 | 0.96 |
| Zinc sulphate heptahydrate | 0.1 | 0.1 | 0.1 | 0.1 |
| Propylene glycol | 0.96 | 0.96 | 0.96 | 0.96 |
| Climbazole | 0.48 | 0.48 | 0.48 | 0.48 |
| Perfume | 0.75 | 0.75 | 0.75 | 0.75 |
| Dimethicone (DC7128)[e] | 0.8 | 0.8 | 0.8 | 0.8 |
| Dimethiconol (DC1788)[f] | 1.2 | 1.2 | 1.2 | 1.2 |
| Phenoxyethanol | 0.5 | 0.5 | 0.5 | 0.5 |
| Sodium salicylate | 0.3 | 0.3 | 0.3 | 0.3 |
| Coco amidopropyl betaine | 1.6 | 1.6 | 1.6 | 1.6 |
| Sodium hydroxide | 0.39 | 0.39 | 0.39 | 0.39 |
| Sodium chloride | 1.2 | 1.2 | 1.2 | 1.2 |

[a]The guar has a DS of 0.14.
[b]The guar has a DS of 0.16.
[c]The guar has a DS of 0.18 and a MW of about 878,000 g/mol.
[d]The guar has a DS of 0.45 and a MW of about 750,000 g/mol.
[e]Commercial dimethicone pre-blended with poloxamer from Dow corning which has a particle size of 10 μm.
[f]Commercial dimethiconol from Dow corning which has a particle size of 0.2 μm.

TABLE 2

| Ingredient | Samples | |
|---|---|---|
| | 4 | 5 |
| Water | Balance | Balance |
| Sodium lauryl ether sulfate (2EO) | 14 | 14 |
| Carbopol 980 | 0.6 | 0.6 |
| Guar hydroxypropyltrimonium chloride[d] | 0.2 | — |
| Guar hydroxypropyltrimonium chloride[g] | — | 0.2 |
| Zinc pyrithione (ZPTO) | 0.96 | 0.96 |
| Zinc sulphate heptahydrate | 0.1 | 0.1 |
| Propylene glycol | 0.96 | 0.96 |
| Climbazole | 0.48 | 0.48 |
| Perfume | 0.75 | 0.75 |
| Dimethicone (DC7128)[e] | 0.8 | 0.8 |
| Dimethiconol (DC1788)[f] | 1.2 | 1.2 |
| Phenoxyethanol | 0.5 | 0.5 |
| Sodium salicylate | 0.3 | 0.3 |
| Coco amidopropyl betaine | 1.6 | 1.6 |
| Sodium hydroxide | 0.39 | 0.39 |
| Sodium chloride | 1.2 | 1.2 |

[g]Commerical guar hydroxypropyltrimonium chloride has a DS of 0.31 and a MW of 500,000 g/mol under the trade name Jaguar Optima from Solvay.

TABLE 3

| Ingredient | Samples | |
|---|---|---|
| | 4 | 6 |
| Water | Balance | Balance |
| Sodium lauryl ether sulfate (2EO) | 14 | 14 |
| Carbopol 980 | 0.6 | 0.6 |
| Guar hydroxypropyltrimonium chloride[d] | 0.2 | — |
| Guar hydroxypropyltrimonium chloride[h] | — | 0.2 |
| Zinc pyrithione (ZPTO) | 0.96 | 0.96 |
| Zinc sulphate heptahydrate | 0.1 | 0.1 |
| Propylene glycol | 0.96 | 0.96 |
| Climbazole | 0.48 | 0.48 |
| Perfume | 0.75 | 0.75 |
| Dimethicone (DC7128)[e] | 0.8 | 0.8 |
| Dimethiconol (DC1788)[f] | 1.2 | 1.2 |
| Phenoxyethanol | 0.5 | 0.5 |
| Sodium salicylate | 0.3 | 0.3 |
| Coco amidopropyl betaine | 1.6 | 1.6 |
| Sodium hydroxide | 0.39 | 0.39 |
| Sodium chloride | 1.2 | 1.2 |

[h]The guar has a DS of 0.58 and a MW of about 1,520,000 g/mol.

Methods

About 0.2 grams of the test sample was taken on artificial skin (VITRO-SKIN from IMS testing group). This was diluted with 1.8 mL water and rubbed with a plastic rod for 30 seconds. The artificial skin surface was then rinsed twice with water, first time with 4 mL water for 30 second and then again with 4 mL water for 30 seconds. The artificial skin was treated five times using the same procedure. The deposition of zinc pyrithione (ZPTO) on the skin was measured using HPLC method.

Results

The results are summarized in Tables 4, 5 and 6 (error represents standard deviation for duplicate measurements).

TABLE 4

| | Samples | | | |
|---|---|---|---|---|
| | 1 | 2 | 3 | 4 |
| ZPTO Deposition (μg/cm$^2$) | 8.17 ± 1.11 | 9.03 ± 0.72 | 7.63 ± 0.59 | 20.62 ± 1.22 |

TABLE 5

| | Samples | |
|---|---|---|
| | 4 | 5 |
| ZPTO Deposition (μg/cm$^2$) | 11.11 ± 1.36 | 3.63 ± 1.08 |

TABLE 6

| | Samples | |
|---|---|---|
| | 4 | 6 |
| ZPTO Deposition (μg/cm$^2$) | 19.59 ± 0.87 | 19.98 ± 3.11 |

The data in Table 4 above indicates that Sample 4 (consistent with the invention) provided significantly better ZPTO deposition ($p<0.05$) compared to Samples 1-3.

The data in Table 5 above also indicates that Sample 4 provided significantly better ZPTO deposition ($p<0.01$) than Sample 5.

The data in Table 6 above indicates that Sample 4 provided parity ZPTO deposition to Sample 6.

Example 2

This example demonstrated the effect of degree of ethoxylation of the anionic surfactant on the deposition of anti-dandruff agent onto the scalp. All ingredients are expressed weight percent of the total formulation, and as level of active ingredient.

TABLE 7

| Ingredient | Samples | | |
|---|---|---|---|
| | 4 | 7 | 8 |
| Water | Balance | Balance | Balance |
| Sodium lauryl ether sulfate (1EO) | — | 14 | — |
| Sodium lauryl ether sulfate (2EO) | 14 | — | — |
| Sodium lauryl ether sulfate (3EO) | — | — | 14 |
| Carbopol 980 | 0.6 | 0.6 | 0.6 |
| Guar hydroxypropyltrimonium chloride[d] | 0.2 | 0.2 | 0.2 |
| Zinc pyrithione (ZPTO) | 0.96 | 0.96 | 0.96 |
| Zinc sulphate heptahydrate | 0.1 | 0.1 | 0.1 |
| Propylene glycol | 0.96 | 0.96 | 0.96 |
| Climbazole | 0.48 | 0.48 | 0.48 |
| Perfume | 0.75 | 0.75 | 0.75 |
| Dimethicone (DC7128)[e] | 0.8 | 0.8 | 0.8 |
| Dimethiconol (DC1788)[f] | 1.2 | 1.2 | 1.2 |
| Phenoxyethanol | 0.5 | 0.5 | 0.5 |
| Sodium salicylate | 0.3 | 0.3 | 0.3 |
| Coco amidopropyl betaine | 1.6 | 1.6 | 1.6 |
| Sodium hydroxide | 0.39 | 0.39 | 0.39 |
| Sodium chloride | 1.2 | 1.2 | 1.2 |

Methods

The same protocol was used to evaluate the deposition of anti-dandruff agent on the scalp as described in Example 1.

Results

The results are summarized in Table 8 (error represents standard deviation for duplicate measurements).

TABLE 8

| | Samples | | |
|---|---|---|---|
| | 4 | 7 | 8 |
| ZPTO Deposition[i] ($\mu g/cm^2$) | $14.94^A \pm 2.26$ | $8.33^B \pm 0.77$ | $11.11^C \pm 2.26$ |

[i]Values with different letter are significantly different ($p < 0.05$).

It can be seen from the results that Sample 4 comprising SLES (2EO) provided significantly better ZPTO deposition efficacy compared to other samples.

The invention claimed is:

1. A hair care composition comprising:
   a) 0.001 to 1% a cationically modified guar polymer having a cationic degree of substitution of from 0.35 to 0.70;
   b) from 0.5 to 45% an ethoxylated alkyl sulfate anionic surfactant having a formula $RO(CH_2CH_2O)nSO_3M$, wherein R is an alkyl or alkenyl group having from 8 to 18 carbon atoms; M is a solubilising cation comprising sodium, potassium, ammonium, substituted ammonium or mixtures thereof; n is the degree of ethoxylation; and
   c) from 0.01 to 10% by weight of an anti-dandruff agent comprising zinc pyrithione, selenium sulfide, or a mixture thereof;
   wherein the degree of substitution is measured using $^1$HNMR and the spectrum is recorded at 25° C.; and
   wherein the degree of ethoxylation of the ethoxylated alkyl sulfate anionic surfactant is 2.

2. The hair care composition according to claim 1, wherein the cationically modified guar polymer is guar hydroxypropyl trimonium chloride.

3. The hair care composition according to claim 1, wherein the cationically modified guar polymer has a cationic degree of substitution of from 0.40 to 0.65.

4. The hair care composition according to claim 1, wherein the cationically modified guar polymer has a molecular weight of from 100,000 g/mol to 2,300,000 g/mol.

5. The hair care composition according to claim 1, wherein R is an alkyl or alkenyl group having from 12 to 18 carbon atoms.

6. The hair care composition according to claim 1, wherein the ethoxylated alkyl sulfate anionic surfactant is sodium lauryl ether sulfate.

7. The hair care composition according to claim 1, wherein the composition comprises the cationically modified guar polymer and the ethoxylated alkyl sulfate anionic surfactant in a weight ratio from 1:200 to 1:1.

8. The hair care composition according to claim 1, wherein the anti-dandruff agent further comprises azole based anti-fungal agents, piroctone olamine or mixtures thereof.

9. The hair care composition according to claim 8, wherein the anti-dandruff agent further comprises climbazole, piroctone olamine or mixtures thereof.

10. The hair care composition according to claim 1, wherein the composition comprises the anti-dandruff agent in an amount of from 0.01 to 5% by weight of the composition.

11. The hair care composition according to claim 1, wherein the composition is a shampoo.

12. A method of depositing anti-dandruff agents onto scalp comprising:
   applying the hair care composition according to claim 1 onto scalp surfaces of an individual; and
   rinsing the scalp surfaces with water.

13. The hair care composition according to claim 3, wherein the cationically modified guar polymer has a cationic degree of substitution of from 0.40 to 0.60.

14. The hair care composition according to claim 4, wherein the cationically modified guar polymer has a molecular weight of from 150,000 g/mol to 2,000,000 g/mol.

15. The hair care composition according to claim 1, wherein the composition comprises the cationically modified guar polymer in an amount of from 0.01 to 0.5%.

16. The hair care composition according to claim 7, wherein the composition comprises the cationically modified guar polymer and the ethoxylated alkyl sulfate anionic surfactant in a weight ratio from 1:150 to 1:10.

17. The hair care composition according to claim 1, wherein the composition comprises the ethoxylated alkyl sulfate anionic surfactant in an amount of from 1 to 30%.

18. The hair care composition according to claim 10, wherein the composition comprises the anti-dandruff agent in an amount of from 0.05 to 2%.

19. A hair care composition comprising:
   a) 0.001 to 1% by weight of guar hydroxypropyl trimonium chloride having a cationic degree of substitution of from 0.35 to 0.70;
   b) 0.5 to 45% of sodium lauryl ether sulfate; wherein the degree of ethoxylation of the sodium lauryl ether sulfate is 2; and
   c) from 0.01 to 5% by weight of an anti-dandruff agent comprising zinc pyrithione, selenium sulfide or a mixture thereof;
   wherein the degree of substitution is measured using $^1$HNMR and the spectrum is recorded at 25° C.

* * * * *